United States Patent [19]

Vignau et al.

[11] 4,307,090
[45] Dec. 22, 1981

[54] NOVEL OXIMES

[75] Inventors: Michael Vignau, Neuilly-sur-Seine; René Heymés, Romainville, both of France

[73] Assignee: Roussel Uclaf, Paris, France

[21] Appl. No.: 115,030

[22] Filed: Jan. 24, 1980

[30] Foreign Application Priority Data

Feb. 9, 1979 [FR] France .............................. 79 03312

[51] Int. Cl.³ .................. A61K 31/545; C07D 501/34
[52] U.S. Cl. ..................................... 424/246; 544/22; 544/26; 544/27; 544/28
[58] Field of Search ..................... 544/28, 22, 26, 27; 424/246

[56] References Cited

FOREIGN PATENT DOCUMENTS 2714880 10/1978 Fed. Rep. of Germany .

Primary Examiner—Paul M. Coughlan, Jr.
Attorney, Agent, or Firm—Hammond & Littell, Weissenberger and Muserlian

[57] ABSTRACT

Novel oximes of the syn isomers of 7-(2-amino-4-thiazolyl)-acetamido-cephalosporanic acid of the formula

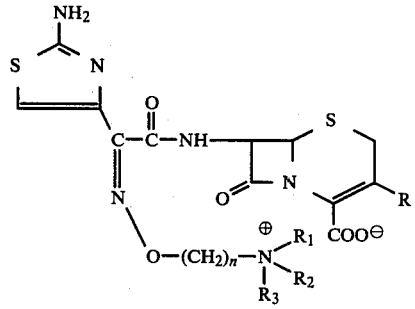

wherein R is selected from the group consisting of hydrogen, chlorine, methoxy, alkyl and alkylthio of 1 to 5 carbon atoms, cycloalkyl of 3 to 5 carbon atoms, acetoxymethyl, carbamoyloxymethyl,

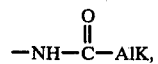

AlK is 1 to 4 carbon atoms, azidomethyl and —CH$_2$—S—R' and R' is selected from the group consisting of a nitrogen heterocycle optionally substituted, acyl of an alkanoic acid of 2 to 4 carbon atoms, 2-oxo-(3H)-thiazolin-4-yl-carbonyl and 3-methyl-1,2-oxazol-5-ylcarbonyl, n is an integer from 2 to 4, $R_1$, $R_2$ and $R_3$ are individually alkyl of 1 to 4 carbon atoms or together taken with the nitrogen atom they are attached to form a group selected from the group consisting of 1,4-diazobicyclo (2,2,2)octan-1-ylium and 1,3,5,7-tetraazatricyclo(3,3,1,1$^{3,7}$) decan-1-ylium and their non-toxic, pharmaceutically acceptable acid addition salts having antibacterial properties and process for their preparation and novel intermediates.

18 Claims, No Drawings

NOVEL OXIMES

STATE OF THE ART

French Pat. Nos. 2,137,899; 2,348,219 and 2,385,722 disclose oximes of syn isomers of ceph-3-eme-4-carboxylic acids.

OBJECTS OF THE INVENTION

It is an object of the invention to provide the novel syn isomers of the compounds of formula I and their non-toxic, pharmaceutically acceptable acid addition salts and a novel process and novel intermediates for their preparation.

It is another object of the invention to provide novel antibacterial compositions and to a novel method of treating or preventing antibacterial infections in warm-blooded animals.

These and other objects and advantages of the invention will become obvious from the following detailed description.

THE INVENTION

The novel oximes of the invention are the syn isomers of 7-(2-amino-4-thiazolyl)-acetamido-cephalosporanic acid of the formula

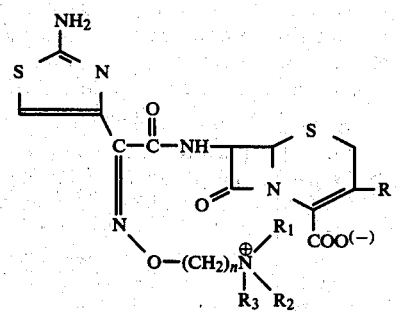

wherein R is selected from the group consisting of hydrogen, chlorine, methoxy, alkyl and alkylthio of 1 to 5 carbon atoms, cycloalkyl of 3 to 5 carbon atoms, acetoxymethyl, carbamoyloxymethyl,

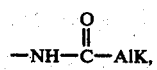

AlK is 1 to 4 carbon atoms, azidomethyl and —CH$_2$—S—R' and R' is selected from the group consisting of a nitrogen heterocycle optionally substituted, acyl of an alkanoic acid of 2 to 4 carbon atoms, 2-oxo-(3H)-thiazolin-4-yl-carbonyl and 3-methyl-1,2-oxazol-5-yl-carbonyl, n is an integer from 2 to 4, R$_1$, R$_2$ and R$_3$ are individually alkyl of 1 to 4 carbon atoms or together taken with the nitrogen atom they are attached to form a group selected from the group consisting of 1,4-diazobicyclo (2,2,2)-octan-1-ylium and 1,3,5,7-tetraazatricyclo(3,3,1,1$^{3,7}$)-decan-1-ylium and their non-toxic, pharmaceutically acceptable acid addition salts.

Examples of R are hydrogen, chlorine, methoxy, alkyl and alkylthio of 1 to 4 carbon atoms such as methyl, ethyl, propyl, isopropyl, butyl, isobutyl, tert.-butyl, pentyl, sec-pentyl, tert.-pentyl, methylthio, ethylthio, propylthio isopropylthio, butylthio, tert.-butylthio, isobutylthio, cycloalkyl such as cyclopropyl, cyclobutyl and cyclopentyl, —CH$_2$—S—R' wherein R' may be acetyl, propionyl or butyryl or a hetero such as 1,2,3-thiadiazolyl, 1,2,5-thiadiazolyl, 1,2,4-thiadiazolyl, 1,3,4-thiadiazolyl, 1H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl or 1,3,4-oxadiazolyl which heteros are optionally substituted with at least one member of the group consisting of methyl, ethyl, propyl, isopropyl, methoxy, ethoxy, propoxy, isopropoxy, amino, hydroxycarbonylmethyl, dimethylaminoethyl and diethylaminoethyl and

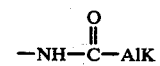

such as acetamido, propionylamido, butyrylamido, isobutyrylamino or valerylamido.

Examples of R$_1$, R$_2$ and R$_3$ as alkyl are methyl, ethyl, propyl, isopropyl, butyl, tert.-butyl and sec-butyl.

Examples of suitable acid for the formation of the acid addition salts are non-toxic, pharmaceutically acceptable organic acids such as sulfuric acid, phosphoric acid, hydrochloric acid, hydroiodic acid, or hydrobromic acid or organic acids such as acetic acid, propionic acid, trifluoroacetic acid, maleic acid, tartaric acid, methanesulfonic acid, benzenesulfonic acid or p-toluene sulfonic acid.

Among the preferred compounds of the invention are those wherein R is hydrogen, those wherein R is methyl, those wherein R is —CH$_2$—S—R" and R" is 1-methyl-1H-tetrazolyl, 1-dimethylaminoethyl-tetrazolyl, 2-methyl-1,3,4-thiadiazolyl, 1,3,4-thiadiazolyl, acetyl, acetoxymethyl, carbamoyloxymethyl or azidomethyl and those wherein R is acetoxymethyl and their non-toxic, pharmaceutically acceptable acid addition salts and those especially wherein n is 2, and those wherein R$_1$, R$_2$ and R$_3$ together with the nitrogen atom to which they are attached form 1,3,5,7-tetraazatricyclo(3,3,1,1$^{3,7}$) decan-1-ylium.

Particularly preferred compounds of the invention are the internal salts of the syn isomer of 3-acetoxymethyl-7-[2-(2-amino-4-thiazolyl)-2-(2-trimethylammonium-ethoxyimino)-acetamido]-ceph-3-eme-4-carboxylic acid or the syn isomer of 3-acetoxymethyl-7-[2-(2-amino-4-thiazolyl)-2-(2-{1,3,5,7-tetraazatricyclo (3,3,1,1$^{3,7}$) decan-1-ylium}-ethoxyimino)-acetamido]-ceph-3-eme-carboxylic acid and their nontoxic, pharmaceutically acceptable acid addition salts.

The products of the invention may exist in the form of a compound of formula I or a compound of the formula

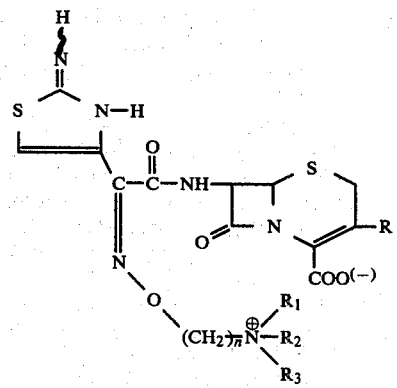

when the products are salified with a mineral or organic acid, the carboxylic group may be in the non-salified —COOH form.

The process of the invention for the preparation of a compound of formula I comprises reacting a compound of the formula

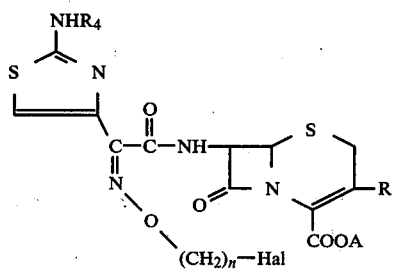

wherein $R_4$ is a protective group for amino, n and R have the above definition, A is selected from the group consisting of hydrogen and an easily removable ester group and Hal is a halogen with a trialkyl amine of the formula

wherein $R_1'$, $R_2'$ and $R_3'$ are alkyl of 1 to 4 carbon atoms or with triethylenediamine or hexamethylenetetraamine to obtain a compound of the formula

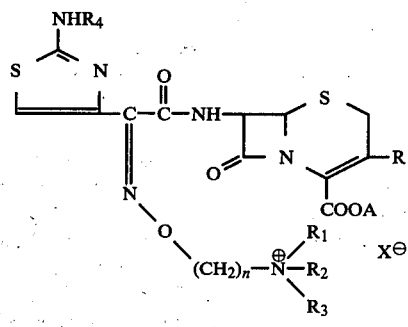

wherein X is an anion and R, $R_1$, $R_2$, $R_3$, $R_4$ and A have the above definitions and reacting the latter with at least one member of the group consisting of hydrolysis agents, hydrogenolysis agents and thiourea to obtain the corresponding compound of formula I which may be salified, if desired.

The protective group $R_4$ may be alkyl of 1 to 6 carbon atoms, especially tert.-butyl or tert.-amyl, aliphatic acyl, aromatic or heterocyclic acyl or a carbamoyl. Examples of lower alkanoyl groups are formyl, acetyl, propionyl, butyryl, isobutyryl, valeryl, isovaleryl, oxalyl, succinyl or pivaloyl. Examples of lower alkoxycarbonyl or cycloalkoxycarbonyl are methoxycarbonyl, ethoxycarbonyl, propoxycarbonyl, 1-cyclopropyle-thoxycarbonyl, isopropoxycarbonyl, butoxycarbonyl, tert.-butoxycarbonyl, pentyloxycarbonyl, tert.-pentyloxycarbonyl, hexyloxycarbonyl. Examples of aromatic acyl groups are benzoyl, toluoyl, naphthoyl, phthaloyl, mesyl, phenylacetyl and phenylpropionyl and benzyloxycarbonyl is in examples of arylalkoxycarbonyl. The acyl groups may be substituted with halogens such as chlorine, bromine, iodine or fluorine, examples of which are chloroacetyl, dichloroacetyl, trichloroacetyl, trifluoroacetyl or bromoacetyl.

$R_4$ may also be arloweralkyl such as benzyl, 4-methoxy-benzyl, phenethyl, trityl, 3,4-dimethoxybenzyl or benzhydryl; or haloalkyl such as trichloroethyl; chlorobenzoyl, p-nitrobenzoyl, p-tert.-butyl-benzoyl, phenoxyacetyl, caprylyl, n-decanoyl, acryloyl, trichloroethoxycarbonyl, methylcarbamoyl, phenylcarbamoyl, naphthylcarbamoyl and the corresponding thiocarbamoyls. The list is not intended to be exhaustive and other amine protective groups may be used such as those known in peptide chemistry.

Among the values for COOA are the easily removable ester groups such as the lower alkyl esters like butyl, isobutyl, tert.-butyl, pentyl and hexyl. Equally useful are acetoxymethyl, propionyloxymethyl, butyryloxymethyl, valeroyloxymethyl, pivaloyloxymethyl, 2-acetoxyethyl, 2-propionyloxyethyl and 2-butyryloxyethyl, 2-mesylethyl, 2-iodoethyl, $\beta,\beta,\beta$-trichloroethyl, vinyl, allyl, ethynyl, propynyl, benzyl, 4-methoxy-benzyl, 4-nitrobenzyl, phenethyl, trityl, diphenylmethyl and 3,4-dimethoxy benzyl esters. Other esters include phenyl, 4-chlorophenyl, tolyl and tert.-butylphenyl esters. The halogen atoms of formula II are preferably bromine or iodine.

The reaction with the tertiary amine or triethylenediamine or hexamethylenetetramine is preferably effected in an organic solvent such as chloroform, hexamethylphosphorotriamide, dimethylformamide, acetone or dioxane and the reaction is preferably effected at room temperature or with slight heating when Hal is bromine or iodine.

The anion of $X^\ominus$ is preferably a halide ion corresponding to Hal when A is an ester group but the anion may also be another anion by the use of an additional reactant. When A of formula II is hydrogen, the compound of formula III is in the form of an interval salt with the carboxylate group acting as the anion.

The transformation of the products of formula III into compounds of formula I is effected by removal of the $R_4$ group and eventually the A group when it is an easily removable ester group. The $R_4$ group may be removed by hydrolysis with an acid or base or by use of hydrazine. It is preferred to use acid hydrolysis to remove optionally substituted alkoxycarbonyl or cycloalkoxycarbonyl group such as tert.-pentyloxycarbonyl or tert.-butyloxycarbonyl or optionally substituted arylalkoxycarbonyl such as benzyloxycarbonyl or trityl or tert.-butyl or 4-methoxy benzyl. The acid which may be an organic or inorganic acid is preferably selected from the group consisting of hydrochloric acid, benzenesulfonic acid, p-toluene sulfonic acid, formic acid or trifluoroacetic acid.

When $R_4$ is an acyl group such as trifluoroacetyl, basic hydrolysis is preferred and the preferred bases are inorganic bases such as alkali metal hydroxides like sodium hydroxide or potassium hydroxide. Also useful are bases such as magnesium hydroxide, baryta or alkali metal bicarbonates and carbonates such as sodium carbonate, sodium bicarbonate, potassium carbonate and potassium bicarbonate, potassium acetate, sodium acetate and other bases.

When hydrazine is used for the hydrolysis, the group to be removed is phthaloyl and the like. A zinc-acetic acid system may be used to remove $R_4$ groups such as trichloroethyl. Groups such as benzhdryl and benzyloxycarbonyl are preferably removed by hydrogenolysis with hydrogen in the presence of a catalyst. The chloroacetyl group is preferably removed with thiourea in a neutral or acidic medium by the reaction of Masaki [J.A.C.S., Vol. 90 (1968), p. 4508]. Other known means for the removal of amine protective groups may also be used.

Preferably, R₄ is selected from the group consisting of trityl, chloroacetyl, tert.-pentyloxycarbonyl, tert.-butoxycarbonyl and benzyloxycarbonyl.

The removal of the A group when it is other than hydrogen is effected under conditions for the removal of the R₄ group such as acid or basic hydrolysis. Acid hydrolysis is used for optionally substituted alkyl or arylalkyl groups and the acid is preferably hydrochloric acid, formic acid, trifluoroacetic acid or p-toluenesulfonic acid, preferably used under moderate conditions, i.e. room temperature or slight heating. Other values of A may be removed by known methods.

When R₄ and A are easily removably of different types, the compounds of formula III may be reacted with a plurality of the above enumerated agents.

The said reactions result in the production of a small amount of the corresponding ceph-2-eme compounds and the said products may be treated by known processes to transform the Δ² compounds into Δ³ compounds. For example, the product containing a Δ² product is oxidized, preferably with a peracid such as m-chloroperbenzoic acid, to obtain the corresponding sulfoxide which is then treated in the presence of water or a hydroxylated solvent to form the corresponding Δ³ sulfoxide which is then reduced in the presence of an acid chloride or phosphorus trichloride. These processes are illustrated in German Pat. No. 1,937,016 or U.S. Pat. No. 3,705,897 and by Kaiser et al [J. Org., Vol. 35 (1970), p. 2430] and Spry et al [J. Org., Vol. 40 (1975), p. 2411].

The salification of the compounds of formula I may be effected with an organic or inorganic acid by the usual method.

A second process of the invention for the preparation of the compounds of formula I comprises reacting a compound of the formula

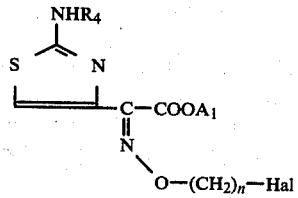

wherein R₄, n and Hal have the above definitions and A₁ is selected from the group consisting of hydrogen and alkyl of 1 to 4 carbon atoms with a trialkylamine

or triethylenediamine or hexamethylene tetraamine wherein R₁, R₂ and R₃ have the above definition and treating the latter with a base when A₁ is alkyl to form a compound of the formula

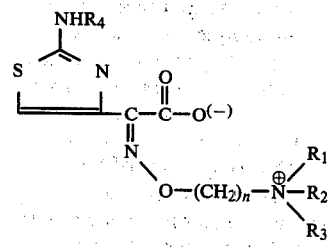

and reacting the compound of formula V or an acid functional derivative thereof with a compound of the formula

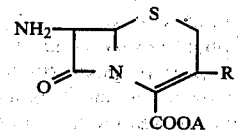

wherein A and R have the above definitions to obtain a compound of formula III which may be treated as above.

The reaction of the amino compounds with the compounds of formula IV is effected under the same conditions for the reaction with the compounds of formula II. The functional derivatives of the acid of formula V may be the acid halide, symetric or mixed anhydride, amide, azide or active ester. Examples of mixed anhydrides are the anhydride formed with isobutyl chloroformate and the active ester may be the ester formed with 2,4-dinitrophenol or 1-hydroxybenzo [1]-triazole. The acid halide is preferably the chloride or bromide and the acid azide or acid amide may also be used.

The acid anhydride may be formed in situ by action with N,N'-disubstituted carbodiimides such as N,N-dicyclohexylcarbodiimide. The acylation reaction is preferably effected in an organic solvent such as methylene chloride although other solvents such as tetrahydrofuran, chloroform or dimethylformamide may also be used.

When the acylation is effected with the acid halide or mixed anhydride with isobutyl chloroformate, the acylation is preferably effected in the presence of a base such as an sodium hydroxide, potassium hydroxide, sodium carbonate, sodium bicarbonate, potassium carbonate, potassium bicarbonate, sodium acetate, triethylamine, pyridine, morpholine or N-methylmorpholine. The reaction is preferably effected at room temperature or below.

The transformation of the products of formula III into the corresponding compounds of formula I may be effected under the above described conditions. The R₄ group is especially trityl, chloroacetyl, tert.-pentyloxycarbonyl, tert.-butoxycarbonyl and benzyloxycarbonyl.

The antibiotic compositions of the invention are comprised of an antibiotically effective amount of at least one compound of formula I and its non-toxic, pharmaceutically acceptable acid addition salts and an inert pharmaceutical carrier or excipient. The compositions may be in the form of tablets, dragees, gelules, granules, suppositories, injectable solutions or suspensions, creams, pomades, gels, etc. prepared in the usual fashion.

Examples of suitable excipients or pharmaceutical carriers are talc, arabic gum, lactose, starch, magnesium stearate, cacao butter, aqueous or non-aqueous vehicles, fatty bodies of vegetable or animal origin, paraffinic derivatives, glycols, preservatives, diverse wetting agents, dispersants and emulsifiers.

The compositions of the invention and particularly those containing the compounds of formula I in the syn form possess very good antibiotic activity against gram positive bacteria such as staphylococcus, streptococcus, particularly penicillin resistant staphylococcus as well as against gram negative bacteria such as coliform bacteria, Klebsiella, Salmonella and Proteus.

The compositions are therefore useful in the treatment of germ sensitive infections and particularly those of staphylococcia such as staphylococcal septicemia, staphylococcia malignant on the face or skin, pyodermatitis, septic or suppurantes sores, anthrax, phlegmons, eresipels, acute primitive or post-grip staphylococcia, bronchopneumonia or pulmonary suppurations. They are equally useful for the treatment of collibacillosis and associated infections, infections of Proteus, Klebsiella and Salmonella and Pseudomonas and other infections caused by gram negative bacteria. They may also be used to desinfect surgical instruments.

Among the preferred antibacterial compositions of the invention are those wherein R is hydrogen, those wherein R is methyl, those wherein R is —$CH_2$—S—R'' and R'' is 1-methyl-1H-tetrazolyl, 1-dimethylaminoethyl-tetrazolyl, 2-methyl-1,3,4-thiadiazolyl, 1,3,4-thiadiazolyl, acetyl, acetoxymethyl, carbamoyloxymethyl or azidomethyl and those wherein R is acetoxymethyl and their non-toxic, pharmaceutically acceptable acid addition salts and those especially wherein n is 2 and those wherein $R_1$, $R_2$ and $R_3$ together with the nitrogen atom to which they are attached form 1,3,5,7-tetraazatricyclo $(3,3,1,1^{3,7})$decan-1-ylium.

Particularly preferred compositions are those where the active ingredient is selected from the group consisting of the internal salts of the syn isomer of 3-acetoxymethyl-7-[2-(2-amino-4-thiazolyl)-2-(2-trimethylammonium ethoxyimino)-acetamido]-ceph-3-eme-4-carboxylic acid or the syn isomer of 3-acetoxymethyl-7-[2-(2-amino-4-thiazolyl)-2-(2-{1,3,5,7-tetraazatricyclo $(3,3,1,1^{3,7})$decan-1-ylium}-ethoxyimino-acetamido]-ceph-3-eme-4-carboxylic acid and their nontoxic, pharmaceutically acceptable acid addition salts.

The novel method of the invention for combatting bacterial infections in warm-blooded animals, including humans, comprises administering to warm-blooded animals an antibacterially effective amount of at least one compound of formula I. The compounds may be administered orally, rectally, parenterally or locally by topical application to the skin or mucous. The usual daily dose is 5 to 80 mg/kg depending the specific compound and method of administration.

The novel intermediate compounds of the invention are the compounds of formulae III and V.

The compounds of formula IV may be prepared by reacting a compound of the formula

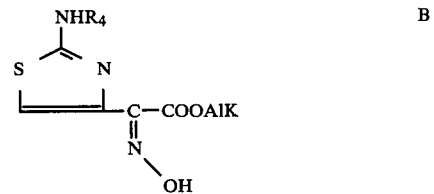

wherein AlK is alkyl of 1 to 4 carbon atoms and $R_4$ has the above definitions with a compound of the formula Hal—$(CH_2)_n$—Hal wherein Hal and n have the above definitions. The said reaction is preferably effected in the presence of a base such as potassium carbonate. The addition is followed by a saponification of the ester group.

The compounds of formula II may be prepared by reacting a compound of formula IV when $A_1$ is hydrogen with a compound of formula VI under conditions similar to the reaction of compounds of formulae V and VI.

Examples of compounds of formula I are those in the following Tables.

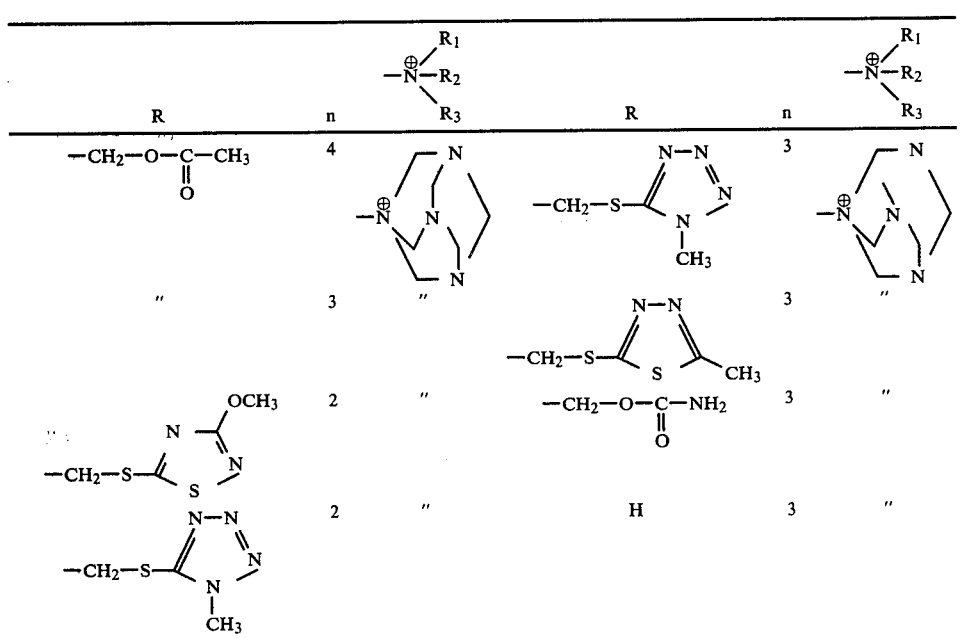

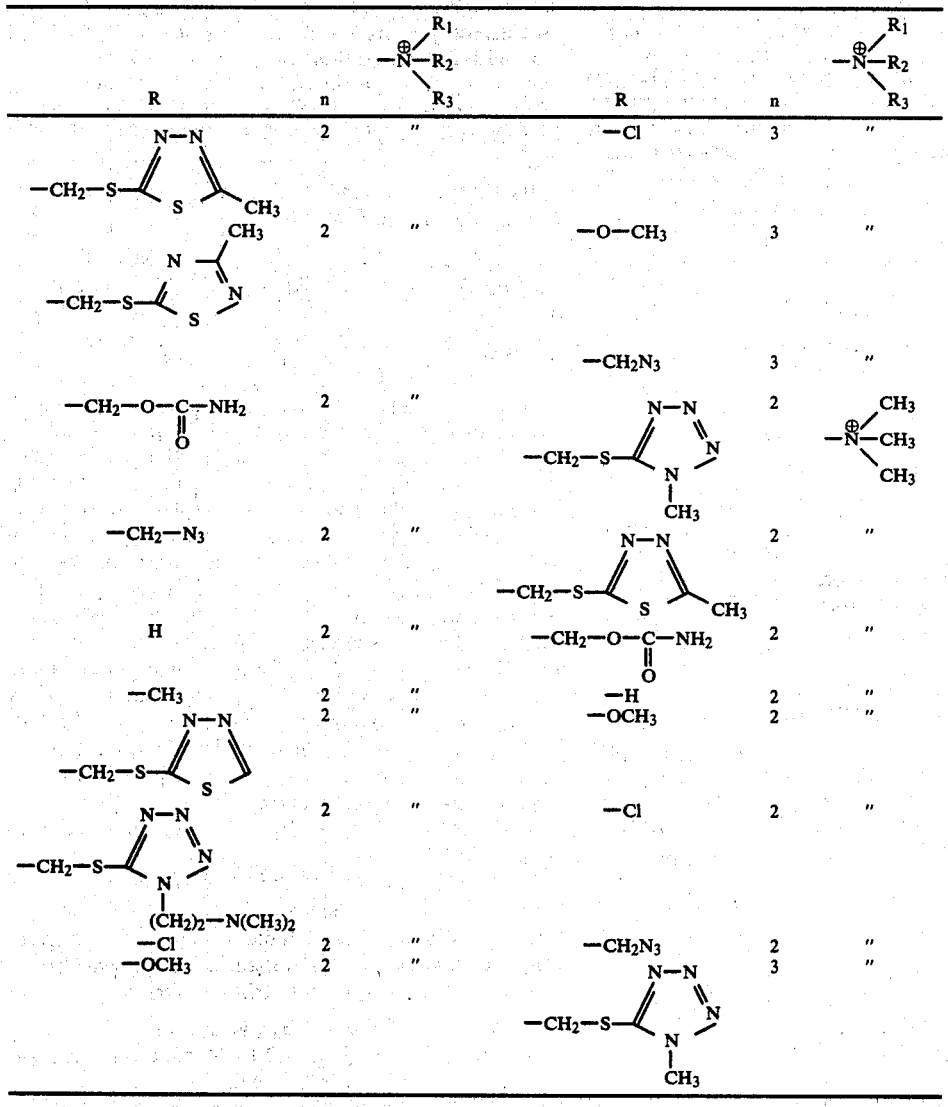

In the following examples there are described several preferred embodiments to illustrate the invention. However, it should be understood that the invention is not intended to be limited to the specific embodiments.

EXAMPLE 1

Syn isomer of the internal salt of 3-acetoxymethyl-7-[2-(2-amino-4-thiazolyl)-2-[2-(1,4-diazabicyclo (2,2,2)-octan-1-ylium]-ethoxyimino]-acetamido-ceph-3-eme-4-carboxylic acid STEP A: Syn isomer of ethyl 2-(2-bromoethoxyimino)-2-(2-tritylamino-4-thiazolyl)-acetate 4.14 g of potassium carbonate were added at room temperature over 3 minutes under an argon atmosphere to a mixture of 4.94 g of the syn isomer of ethyl 2-hydroxyimino-2-(2-tritylamino-4-thiazolyl)-acetate in 10 ml of dimethylformamide and after stirring the mixture at 20° C. for 20 minutes, 8.65 ml of 1,2-dibromoethane were added thereto. The mixture was stirred for 30 hours and was then poured into a mixture of 100 ml of distilled water and 20 ml of methylene chloride. The decanted aqueous phase was extracted with methylene chloride and the combined organic phases were washed with water, dried and evaporated to dryness. The residue was chromatographed over silica gel and was eluted with benzene containing 5% of ether to obtain a first fraction which was dissolved at 50° to 60° C. in methanol and crystallized at 0° C. to 5° C. The mixture was vacuum filtered to obtain 1.16 g of syn isomer of ethyl 2-(2-bromoethoxyimino)-2-(2-tritylamino-4-thiazolyl)-acetate in the form of a cream white product melting at 117° C. There was obtained a homogenous fraction of 1.258 g.

STEP B: Syn isomer of ethyl 2-(2-iodoethoxyimino)-2-(2-tritylamino-4-thiazolyl)-acetate A mixture of 6 g of the product of Step A, 60 ml of methyl ethyl ketone and 2.141 g of sodium iodide was refluxed for 70 minutes and was then evaporated to dryness under reduced pressure. The residue was taken up in 120 ml of methylene chloride and the organic phase was washed several times with water. The wash waters were extracted with methylene chloride and the combined organic phases were dried and evaporated to dryness. The residue was crystallized from ether and the product was dried under reduced pressure to obtain 6.22 g of syn isomer of ethyl 2-(2-iodoethoxyimino)-2-(2-tritylamino-4-thiazolyl)-acetate melting at 110° C.

STEP C: Iodide of the syn isomer of ethyl 2-(2-tritylamino-4-thiazolyl)-2-[2-(1,4-diazabicyclo (2,2,2)-octan-1-ylium)-ethoxyimino]-acetate A solution of 611 mg of the product of Step B, 123 mg of triethylenediamine and 1 ml of acetone was stirred for 18 hours at room temperature and was then vacuum filtered. The recovered product was washed with acetone and ether to obtain 600 mg of the iodide of the syn isomer of ethyl 2-(2-tritylamino-4-thiazolyl)-2-[2-(1,4-diazabicyclo-(2,2,2)-octan-1-ylium)-ethoxyimino]-acetate melting at 185° C. and which after resolidification melted at 260° C.

MNR (Spectrum [(CD$_3$)$_2$SO$_2$]: triplet at 1.1 ppm J=7 Hz and double doublet at 3.98 ppm J=7 Hz (COOEt); 2.83 to 3.66 ppm (CH$_2$—N); 7.03 ppm (syn H$_5$ thiazole).

IR Spectrum (nujol): CO ester at 1726 cm$^{-1}$; heterocycle at 1531 cm$^{-1}$.

UV Spectrum (0.1 N HCl in ethanol): Max. at 270 nm; E$_1^1$=156.

STEP D: Syn isomer of internal salt of 2-(2-tritylamino-4-thiazolyl)-2-[2-(1,4-diazabicyclo-(2,2,2)-octan-1-ylium)-ethoxyimino]-acetic acid 6.45 ml of N sodium hydroxide solution were added to a solution of 4.2 g of reproduct of Step C in 42 ml of dimethylsulfoxide and after standing overnight at room temperature, the solution was poured into 300 ml of benzene. The mixture was stirred for one hour and was vacuum filtered and the recovered product was washed with benzene, with ether and finally with isopropyl ether to obtain 3.55 g of raw syn isomer of internal salt of 2-(2-tritylamino-4-thiazolyl)-2-[2-(1,4-diazabicyclo-(2,2,2)-octan-1-ylium)-ethoxyimino]-acetic acid melting at ≈262° C. with decomposition.

NMR Spectrum: (DCl, D$_2$O, CD$_3$—$\overset{O}{\overset{\|}{C}}$—CD$_3$):

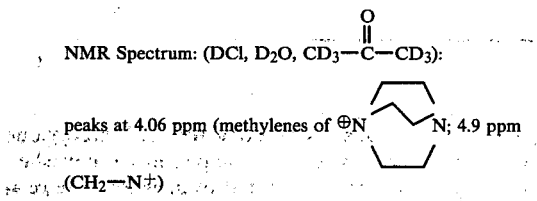

peaks at 4.06 ppm (methylenes of $\oplus$N⌒N; 4.9 ppm (CH$_2$—N+).

IR Spectrum (nujol): COO$^-$ at 1621 cm$^{-1}$; thiazolic heterocyclic at 1547 cm$^{-1}$.

UV Spectrum (0.1 N HCl methanol): Max. at 276 nm; E$_1^1$=198.

STEP E: Iodide of syn isomer of benzhydryl-3-acetoxymethyl-7-[2-(2-tritylamino-4-thiazolyl)-2-{2-(1,4-diazabicyclo (2,2,2)-octan-1-ylium)-ethoxyimino}-acetamido]-ceph-3-eme-4-carboxylate A solution of 1 g of the product of Step D, 0.288 g of pyridine hydroiodide, 0.573 g of dicyclohexylcarbodiimide, 0.548 g of benzhydryl 3-acetoxymethyl-7-amino-ceph-3-eme-4-carboxylate and 5.5 ml of dimethylformamide was stirred at room temperature for 20 minutes and was then vacuum filtered. 60 ml of water were added to the filtrate to cause precipitation and the mixture was vacuum filtered. The recovered product was rinsed with water and dissolved in 20 ml of chloroform. The organic phase was washed with water, dried and evaporated to dryness and the residue was triturated with 12 ml of ether. The mixture was vacuum filtered and the product was rinsed with ether to obtain 1.247 g of raw iodide of syn isomer of benzhydryl 3-acetoxymethyl-7-[2-(2-tritylamino-4-thiazolyl)-2-{2-(1,4-diazabicyclo (2,2,2) octan-1-ylium)-ethoxyimino}-acetamido]-ceph-3-eme-4-carboxylate melting at ≈186° C. with decomposition.

STEP F: Syn isomer of internal salt of 3-acetoxymethyl-7-[2-(2-amino-4-thiazolyl)-2-(2-{1,4-diazabicyclo [2,2,2]-octan-1-ylium}-ethoxyimino)-acetamido]-ceph-3-eme-4-carboxylic acid A mixture of 1.24 g of the product of Step E in 5 ml of trifluoroacetic acid was stirred for 3 minutes at room temperature and was then vacuum filtered. The filter was rinsed with trifluoroacetic acid and the filtrate was poured into 50 ml of iced ether. The mixture was vacuum filtered and the recovered product was dissolved in 1.1 ml of methanol. 12 ml of ether were added to the solution and the mixture was stirred at room temperature for 5 minutes and was vacuum filtered. The recovered product was empasted with ethanol and was vacuum filtered. The product was rinsed with ethanol and then with ether to obtain 324 mg of syn isomer of internal salt of 3-acetoxymethyl-7-[2-(2-amino-4-thiazolyl)-2-(2-{1,4-diazabicyclo-[2,2,2]-octan-1-ylium}-ethoxyimino)-acetamido]-ceph-3-eme-4-carboxylic acid melting at ≈235° C. with decomposition.

NMR Spectrum (dimethylsulfoxide): peaks at 6.83 ppm (H$_5$ of thiazole); at 2.03 ppm (OAc).

IR Spectrum (nujol): C=O of β-lactam at 1778 cm$^{-1}$; C=O of acetyloxy at 1724 cm$^{-1}$; COO$^-$ at 1632 cm$^{-1}$.

UV Spectrum (0.1 N HCl in ethanol): Max. at 221 nm; Max. at 261 nm.

EXAMPLE 2

Syn isomer of 3-acetoxymethyl-7-[2-(2-amino-4-thiazolyl)-2-(2-trimethylammoniumethoxyimino)-acetamido]-ceph-3-eme-4-carboxylic acid trifluoroacetate STEP A: Syn isomer of 2-(2-iodoethoxyimino)-2-(2-tritylamino-4-thiazolyl)-acetic acid 5.5 ml of 2 N sodium hydroxide solution were added dropwise under an inert atmosphere to a mixture of 6.7 g of the syn isomer of ethyl 2-(2-iodoethoxyimino)-2-(2-tritylamino-4-thiazolyl)-acetate, 5.5 ml of dioxane and 44 ml of absolute ethanol and then 7 ml of absolute ethanol were added. The mixture was stirred overnight at room temperature and was then vacuum filtered to remove the sodium salt of the said acid. The sodium salt was rinsed twice with 3 ml of a 4-1 ethanol-dioxane mixture and was evaporated with ether. The product was added to 100 ml of water and 100 ml of chloroform and the pH was adjusted to 2 by addition of 1 N hydrochloric acid. The decanted organic phase was washed with a saturated aqueous sodium chloride solution, dried and evaporated to dryness under reduced pressure. The resin was dissolved at 40° C. in 35 ml of dichloroethane and crystallization was induced. The mixture returned to room temperature over 72 hours and was vacuum filtered. The recovered product was rinsed and dried to obtain 5.4 g of a white product solvated with dichloroethane which was equivalent to 4.61 g pure syn isomer of 2-(2-iodoethoxyimino)-2-(2-tritylamino-4-thiazolyl)-acetic acid melting at 161° C.

UV Spectrum (0.1 N HCl in ethanol): Max. at 278 nm; $E_1^1=235$.

NMR Spectrum (CDCl$_3$): peak at 6.58 ppm (5-proton of thiazole).

STEP B: Syn isomer of internal salt of 2-(2-tritylamino-4-thiazolyl)-2-(2-trimethylammonium-ethoxyimino)-acetic acid A mixture of 2.34 g of the solvate of Step A and 12 ml of N-methylpyrrolidone was stirred at room temperature for 5 minutes for total dissolution and then a current of trimethylamine was bubbled therethrough for an hour. Crystallization was induced and the mixture was allowed to stand at room temperature for 3 hours. Then 30 ml of acetone were added thereto dropwise and the mixture was stirred for 30 minutes and was then vacuum filtered to obtain 1.42 g of syn isomer of internal salt of 2-(2-tritylamino-4-thiazolyl)-2-(2-trimethylammonium-ethoxyimino)-acetic acid melting at ≃265° C. with decomposition.

NMR Spectrum (dimethylsulfoxide): peaks at 3.12 ppm (methyls of -N$^{\oplus}$-(CH$_3$)$_3$); at 3.5 ppm (CH$_2$-N$^{\oplus}$-); at 6.6 ppm (H$_5$ of syn thiazole).

UV Spectrum (0.1 N HCl in ethanol): Max. at 277 nm; $E_1^1=263$.

STEP C: Syn isomer of iodide of benzyhydryl 3-acetoxymethyl-7-[2-(2-tritylamino-4-thiazolyl)-2-(2-trimethylammonium ethoxyimino)-acetamido]-ceph-3-eme-4-carboxylate A mixture of 820 mg of the product of Step B, 332 mg of pyridine hydroiodide, 560 mg of benzhydryl 3-acetoxymethyl-7-amino-ceph-3-eme-4-carboxylate, 660 mg of dicyclohexylcarbodiimide and 8 ml of dimethylformamide was vigorously stirred at room temperature for 20 minutes and was vacuum filtered to remove dicyclohexylurea. The filtrate was poured into 170 ml of ethyl and the mixture was triturated. The liquid was decanted and the gummy residue was added to 10 ml of ether. The mixture was stirred for 15 minutes at room temperature and was vacuum filtered to obtain 1.3 g of product. The latter was chromatographed over silica gel and was eluted with a 9-1 methylene chloride-methanol mixture to obtain 900 mg of white syn isomer of iodide of benzhydryl 3-acetoxymethyl-7-[2-(2-tritylamino-4-thiazolyl)-2-(2-trimethylammonium ethoxyimino)-acetamido]-ceph-3-eme-4-carboxylate melting at 210° C. with decomposition.

NMR Spectrum (CDCl$_3$): peaks at 2 ppm (OAc); at 3.32 ppm (methyls of $\oplus$N(CH$_3$)$_3$); at 4.03 ppm ($\oplus$NCH$_2$); 6.4 ppm (H$_5$ of thiazole syn); at 6.93 ppm (benzyl).

UV Spectrum (0.1 N HCl in ethanol): Max. at 268 nm; $E_1^1=167$.

IR Spectrum (CHCl$_3$): C═O of β-lactam at 1780 cm$^{-1}$; heterocycle+amide II at 1526 cm$^{-1}$; C═O ester and OAc at 1739 and 1731 cm$^{-1}$.

STEP D: Syn isomer of trifluoroacetate of 3-acetoxymethyl-7-[2-(2-amino-4-thiazolyl)-2-(2-trimethylammoniumethoxyimino)-acetamido]-ceph-3-eme-4-carboxylic acid A mixture of 400 mg of the product of Step C in 2.4 ml of trifluoroacetic acid was stirred for 3 minutes at room temperature and was then vacuum filtered. The filter was rinsed with 0.2 ml of trifluoroacetic acid and the filtrate was mixed with 30 ml of a 1—1 ether-isopropyl ether mixture. The mixture was stirred at room temperature and was vacuum filtered and the hydroscopic product was taken up in 0.6 ml of methanol. 6 ml of ether were added to cause precipitation and the mixture was stirred at room temperature for 15 minutes and was vacuum filtered. The product was rinsed with ether to obtain 202 mg of syn isomer of trifluoroacetate of 3-acetoxymethyl-7-[2-(2-amino-4-thiazolyl)-2-(2-trimethylammoniumethoxyimino)-acetamido]-ceph-3-eme-4-carboxylic acid melting at ≃240° C. with decomposition.

NMR Spectrum (dimethylsulfoxide): peaks at 2.03 ppm (OAc); at 3.13 ppm (methyls of -N$^{\oplus}$(CH$_3$)$_3$); at 6.87 ppm (H$_5$ of thiazole syn).

UV Spectrum (0.1 N HCl in ethanol): Max. at 261 nm; $E_1^1=275$.

EXAMPLE 3

Mixture of trifluoroacetate and iodide of syn isomer of 3-acetoxymethyl-7-[2-(2-amino-4-thiazolyl)-2-(2-{1,3,5,7-tetrazatricyclo-(3,3,1,1$^{3,7}$)-decan-1-ylium}-ethoxyimino)-acetamido]-ceph-3-eme-4-carboxylic acid

STEP A: Syn isomer of internal salt of 3-acetoxymethyl-7-[2-(2-tritylamino-4-thiazolyl)-2-(2-{1,3,5,7-tetrazatricyclo (3,3,1,1$^{3,7}$)-decan-1-ylium}-ethoxyimino)-acetamido]-ceph-3-eme-4-carboxylic acid A mixture of 8.4 g of methanamine, 30 ml of tetrachloroethane and 3.5 g of the isopropyl ether solvate of the syn isomer of 2-(2-tritylamino-4-thiazolyl)-2-(2-iodoethoxyimino)-acetic acid (equivalent of 3 g of pure acid) was stirred at room temperature for 4 days and isopropyl ether was added to cause precipitation. The mixture was stirred for 30 minutes and was vacuum filtered. The product was rinsed with ether and was taken up in 110 ml of chloroform. The mixture was stirred for 30 minutes and was vacuum filtered to obtain 4.8 g of raw syn isomer of internal salt of 3-acetoxymethyl-7-[2-(2-tritylamino-4-thiazolyl)-2-(2-{1,3,5,7-tetrazatricyclo (3,3,1,1$^{3,7}$)-decan-1-ylium}-ethoxyimino)-acetamido]-ceph-3-eme-4-carboxylic acid melting at 228° C. with decomposition. The product was taken up in 10 ml of chloroform and the mixture was stirred for 30 minutes and was vacuum filtered. The product was rinsed with chloroform and was taken up in water. The mixture was stirred for 30 minutes and was vacuum filtered and the product was empasted with 100% ethanol. The mixture was vacuum filtered and the product was rinsed with 2 ml of ethanol and then 2 ml of ether to obtain 2.9 g of the desired compound melting at 212° C. with decomposition.

NMR Spectrum (dimethylsulfoxide): peaks at 5.17 ppm (methylenes of —N$^{\oplus}$—CH$_2$—N); at 6.63 ppm (H$_5$ of syn thiazole); at 7.3 ppm (trityl).

UV Spectrum (0.1 N HCl in ethanol): Max. at 276 nm; $E_1^1=216$.

IR Spectrum (nujol): COO⁻ at 1490 cm⁻¹; heterocycle at 1534–1523 cm⁻¹.

STEP B: Syn isomer of iodide of benzhydryl 3-acetoxy-methyl-7-[2-(2-tritylamino-4-thiazolyl)-2-(2-{1,3,5,7-tetrazatricyclo (3,3,1,1³,⁷)-decan-1-ylium}-ethoxyimino)-acetamido]-ceph-3-eme-4-carboxylate A mixture of 0.267 g of the product of Step A, 0.1 g of pyridine hydroiodide, 0.22 g of dicyclohexylcarbodiimide, 0.22 g of pure benzhydryl 3-acetoxymethyl-7-amino-ceph-3-eme-4-carboxylate and 2 ml of anhydrous dimethylformamide was stirred at room temperature and was then vacuum filtered to remove cyclohexylurea. 20 ml of ether were added to the filtrate and the mixture was stirred for 30 minutes and was then vacuum filtered. The product was rinsed with ether to obtain 865 mg of product which was chromatographed over silica gel. Elution with an 8-2 chloroform-methanol mixture yielded 0.39 g of syn isomer of iodide of benzhydryl 3-acetoxy-methyl-7-[2-(tritylamino-4-thiazolyl)-2-(2-{1,3,5,7-tetrazatricyclo (3,3,1,1³,⁷)-decan-1-ylium}-ethoxyimino-acetamido]-ceph-3-eme-4-carboxylate melting at 216° C. with decomposition.

UV Spectrum (0.1 N HCl in ethanol): Max. at 268 nm; $E_1^1 = 159$; $\epsilon = 18,200$.

IR Spectrum (CHCl₃): C=O of β-lactam at 1778 cm⁻¹; C=O of amide at 1671 cm⁻¹; C=NOR at 1064 cm⁻¹.

STEP C: Mixture of trifluoroacetate and iodide of syn isomer of 3-acetoxymethyl-7-[2-(2-amino-4-thiazolyl)-2-(2-{1,3,5,7-tetrazatricyclo (3,3,1,1³,⁷)-decan-1-ylium}-ethoxyimino)-acetamido]-ceph-3-eme-4-carboxylic acid 300 mg of the product of Step B in 3 ml of trifluoroacetic acid was triturated for 40 seconds and was then vacuum filtered. 30 ml of ether were added to the filtrate and the mixture was stirred for 5 minutes and was then vacuum filtered. The filter was rinsed with ether and the very hygroscopic product was taken up in 0.6 ml of methanol. 6 ml of ether were added and the mixture was stirred for 5 minutes and was then vacuum filtered. The filter was rinsed with ether and the very hygroscopic product was taken up in 0.6 ml of methanol, 6 ml of ether were added and the mixture was stirred for 5 minutes at room temperature and was vacuum filtered. The product was rinsed with ether to obtain 100 mg of white mixture of trifluoroacetate and iodide of syn isomer of 3-acetoxymethyl-7-[2-(2-amino-4-thiazolyl)-2-(2-{1,3,5,7-tetrazatricyclo (3,3,1,1³,⁷)-decan-1-ylium}-ethoxyimino)-acetamido]-ceph-3-eme-4-carboxylic acid melting at 221° C. with decomposition.

NMR Spectrum (dimethylsulfoxide): peaks at 2.03 ppm (OAc); at 4.53 and 5.12 ppm (CH₂ of methanamine); at 6.85 ppm (H₅ of thiazole syn).

IR Spectrum (nujol): C=O of β-lactam at 1775 cm⁻¹; C=O of amide at 1672 cm⁻¹.

EXAMPLE 4

Injectable solutions were prepared with 500 mg of the syn isomer of 3-acetoxymethyl-7-[2-(2-amino-4-thiazolyl)-2-(2-{1,3,5,7-tetrazabicyclo (3,3,1,1³,⁷)-decan-1-ylium}-ethoxyimino)-acetamido]-ceph-3-eme-4-carboxylic acid or the syn isomer of 3-acetoxymethyl-7-[2-(2-amino-4-thiazolyl)-2-(2-{1,3,5,7-trimethylammonium}ethoxyimino)-acetamido]-ceph-3-eme-4-carboxylic acid and sufficient sterile aqueous excipient for a final volume of 5 ml. Gelules were prepared containing 250 mg of either one of the said compounds and sufficient excipient for a final weight of 400 mg.

PHARMACOLOGICAL DATA

A. In Vitro Activity

The method used was a dilution of a liquid medium where a series of tubes received the same quantity of a sterile nutritive media and increasing doses of the test compounds were placed therein. Then each tube was seeded with a bacterial strain and was incubated for 24 to 48 hours at 37° C. in an oven. The increasing inhibition was determined by transillumination to determine the minimum inhibiting concentration (MIC in μg/ml) and the results are reported in the following Table.

| PRODUCT OF EXAMPLE 3 | | |
|---|---|---|
| | M.I.C. in μg/ml | |
| STRAINS | 24 H | 48 H |
| Staphylococcus aureus ATCC 6 538 Pen-Sensible | 10 | 10 |
| Staphylococcus aureus UC 1 128 Pen-Résistant | 10 | 10 |
| Staphylococcus aureus exp. n° 54 146 | 8 | 10 |
| Streptococcus pyogènes A 561 | 0,02 | 0,02 |
| Streptococcus faecalis 5 432 | 10 | >40 |
| Streptococcus faecalis 99 F 74 | >40 | >40 |
| Bacillus subtilis ATCC 6 633 | 2 | 3 |
| Escherichia coli Sensible Tétracycline ATCC 9 637 | 0,5 | 0,5 |
| Escherichia coli Résistant Tétracycline ATCC 11 303 | 0,05 | 0,1 |
| Escherichia coli Exp. TO₂₆B₆ | 0,1 | 0,1 |
| Escherichia coli Résistant Gentamycine, Tobramycine R 55 123 D | 0,1 | 0,2 |
| Klebsiella pneumoniae Exp. 52 145 | 0,05 | 0,05 |
| Klebsiella pneumoniae 2 536 Résistant Gentamycine | 0,5 | 0,5 |
| Proteus mirabilis (indol −) A 235 | 0,1 | 0,2 |
| Proteus vulgaris (indol +) A 232 | 1 | 2 |
| Salmonella typhimurium 420 | 0,1 | 0,3 |
| Enterobacter cloacae 681 | 5 | 5 |
| Providencia Du 48 | 1 | 1 |
| Serratia Résistant Gentamycine 2 532 | 0,5 | 0,5 |

Various modifications of the products and processes of the invention may be made without departing from the spirit or scope thereof and it is to be understood that the invention is intended to be limited only as defined in the appended claims.

We claim:

1. A compound selected from the group consisting of the syn isomers of 7-(2-amino-4-thiazolyl)-acetamido-cephalosporanic acid of the formula

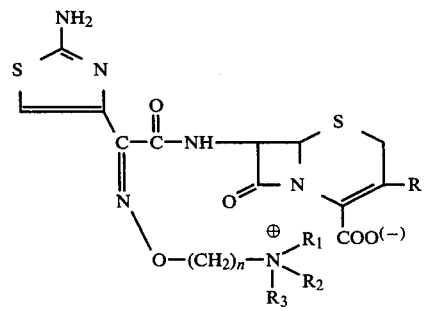

wherein R is selected from the group consisting of hydrogen, chlorine, methoxy, alkyl and alkylthio of 1 to 5 carbon atoms, cycloalkyl of 3 to 5 carbon atoms, acetoxymethyl, carbamoyloxymethyl,

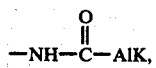

AlK is 1 to 4 carbon atoms, azidomethyl and —CH₂—S—R' and R' is selected from the group consisting of 1,2,3-thiadiazolyl, 1,2,5-thiadiazolyl, 1,2,4-thiadiazolyl, 1,3,4-thiadiazolyl, 1H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl or 1,3,4-oxadiazolyl which heteros are optionally substituted with at least one member of the group consisting of methyl, ethyl, propyl, isopropyl, methoxy, ethoxy, propoxy, isopropoxy, amino, hydroxycarbonylmethyl, dimethylaminoethyl and diethylaminoethyl and

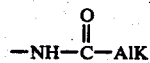

and AlK is alkyl of up to 5 carbon atoms, acyl of an alkanoic acid of 2 to 4 carbon atoms, 2-oxo-(3H)-thiazolyl-4-yl-carbonyl and 3-methyl-1,2-oxazol-5-yl-carbonyl, n is an integer from 2 to 4 R₁, R₂ and R₃ are individually alkyl of 1 to 4 carbon atoms or together taken with the nitrogen atom they are attached to form a group selected from the group consisting of 1,4-diazobicyclo-(2,2,2)-octan-1-ylium and 1,3,5,7-tetrazatricyclo-(3,3,1,1³,⁷) decan-1-ylium and their non-toxic, pharmaceutically acceptable acid addition salts.

2. A compound of claim 1 wherein R is selected from the group consisting of hydrogen, methyl, azidomethyl, acetoxymethyl, carbamoyloxymethyl and —CH₂—SR" and R" is selected from the group consisting of 1-methyl-(1H)-tetrazolyl, 2-methyl-1,3,4-thiadiazolyl, 1,3,4-thiadiazolyl, acetyl and 1-dimethylaminoethyl-tetrazolyl.

3. A compound of claim 1 wherein R is acetoxymethyl.

4. A compound of claim 1 wherein R₁, R₂ and R₃ together with the nitrogen atom to which they are attached form 1,3,5,7-tetrazatricyclo-(3,3,1,1³,⁷) decan-1-ylium.

5. A compound of claim 1 selected from the group consisting of the syn isomer of the internal salt of 3-acetoxymethyl-7-[2-(2-amino-4-thiazolyl)-2-(2-trimethylammonium-ethoxyimino)-acetamido]-ceph-3-eme-4-carboxylic acid and its non-toxic, pharmaceutically acceptable acid addition salts.

6. A compound of claim 1 selected from the group consisting of the syn isomer of the internal salt of 3-acetoxymethyl-7-[2-(2-amino-4-thiazolyl)-2-(2-{1,3,5,7-tetrazatricyclo-(3,3,1,1³,⁷)-decan-1-ylium}-ethoxyimino)-acetamido]-ceph-3-eme-4-carboxylic acid and its non-toxic, pharmaceutically acceptable acid addition salts.

7. An antibacterial composition comprising an antibacterially effective amount of at least one compound of claim 1 and a pharmaceutical carrier.

8. A composition of claim 7 wherein R is selected from the group consisting of hydrogen, methyl, azidomethyl, acetoxymethyl, carbamoyloxymethyl and —CH₂—SR" and R" is selected from the group consisting of 1-methyl-(1H)-tetrazolyl, 2-methyl-1,3,4-thiadiazolyl, 1,3,4-thiadiazolyl, acetyl and 1-dimethylaminoethyl-tetrazolyl.

9. A composition of claim 7 wherein R is acetoxymethyl.

10. A composition of claim 7 wherein R₁, R₂ and R₃ together with the nitrogen atom to which they are attached form 1,3,5,7-tetrazatricyclo-(3,3,1,1³,⁷)-decan-1-ylium.

11. A composition of claim 7 wherein the compound is selected from the group consisting of syn isomer of the internal salt of 3-acetoxymethyl-7-[2-(2-amino-4-thiazolyl)-2-(2-trimethylammonium-ethoxyimino)-acetamido]-ceph-3-eme-4-carboxylic acid and its non-toxic, pharmaceutically acceptable acid addition salts.

12. A composition claim 7 wherein the compound is selected from the group consisting of the syn isomer of the internal salt of 3-acetoxymethyl-7-[2-(2-amino-4-thiazolyl)-2-(2-{1,3,5,7-tetrazatricyclo-(3,3,1,1³,⁷)-decan-1-ylium}-ethoxyimino)-acetamido]-ceph-3-eme-4-carboxylic acid and its non-toxic, pharmaceutically acceptable acid addition salts.

13. A method of treating bacterial infections in warm-blooded animals comprising administering to warm-blooded animals an antibacterially effective amount of at least one compound of claim 1.

14. A method of claim 13 wherein R is selected from the group consisting of hydrogen, methyl, azidomethyl, acetoxymethyl, carbamoyloxymethyl and —CH₂—SR" and R" is selected from the group consisting of 1-methyl-(1H)-tetrazolyl, 2-methyl-1,3,4-thiadiazolyl, 1,3,4-thiadiazolyl, acetyl and 1-dimethylaminoethyl-tetrazolyl.

15. A method of claim 13 wherein R is acetoxymethyl.

16. A method of claim 13 wherein R₁, R₂ and R₃ together with the nitrogen atom to which they are attached form 1,3,5,7-tetrazatricyclo-(3,3,1,1³,⁷)-decan-1-ylium.

17. A method of claim 13 wherein the compound is selected from the group consisting of the syn isomer of the internal salt of 3-acetoxymethyl-7-[2-(2-amino-4-thiazolyl)-2-(2-trimethylammonium-ethoxyimino)-acetamido]-ceph-3-eme-4-carboxylic acid and its non-toxic, pharmaceutically acceptable acid addition salts.

18. A method of claim 13 wherein the compound is selected from the group consisting of the syn isomer of the internal salt of 3-acetoxymethyl-7-[2-(2-amino-4-thiazolyl)-2-(2-{1,3,5,7-tetrazatricyclo-(3,3,1,1³,⁷)-decan-1-ylium}-ethoxyimino)-acetamido]-ceph-3-eme-4-carboxylic acid and its non-toxic, pharmaceutically acceptable acid addition salts.

* * * * *

UNITED STATES PATENT AND TRADEMARK OFFICE
CERTIFICATE OF CORRECTION

PATENT NO. : 4,307,090

DATED : Dec. 22, 1981

INVENTOR(S) : Michel Vignau and Rene Heymes

It is certified that error appears in the above—identified patent and that said Letters Patent is hereby corrected as shown below:

Title page [75]: The first inventor's name "Michael Vignau" should read
--Michel Vignau--

Col. 2, line 40; Col. 7, lines 32 and 40; Col. 12, line 6; Col. 14, line 49; Col. 17, line 45, Col. 18, lines 13 and 43:
"acetox" should read --acetoxy- --

Col. 2, line 41; Col. 7, lines 32, 33 and 41; Col. 12, line 7; Col. 14, line 50 Col. 17, line 46; Col. 18, lines 14 and 44;
"ymethyl" should read --methyl--

Col. 12, line 30; Col. 14, line 51; Col. 17, line 61:
"ethox-" should read --ethoxy--

Col. 12, line 31; Col. 14, line 52; Col. 17, line 62: "yimino" should read
--imino--

Col. 4, line 67: "benzylox-" should read --benzyloxy- --
Col. 4, line 68; Col. 6, line 57: "ycarbonyl" should read --carbonyl--
Col. 5, line 20: "removably" should be --removable--
Col. 6, line 56: "pentylox-" should read --pentyloxy- --
Col. 7, line 31: "carbamoylox-" should read --carbamoyloxy- --

Signed and Sealed this

Eleventh Day of May 1982

[SEAL]

Attest:

GERALD J. MOSSINGHOFF

*Attesting Officer*     *Commissioner of Patents and Trademarks*